United States Patent [19]
Cho

[11] Patent Number: 4,802,461
[45] Date of Patent: Feb. 7, 1989

[54] RIGID ENDOSCOPE WITH FLEXIBLE TIP

[75] Inventor: George Cho, Sudbury, Mass.

[73] Assignee: Candela Laser Corporation, Wayland, Mass.

[21] Appl. No.: 89,579

[22] Filed: Aug. 26, 1987

[51] Int. Cl.⁴ ............................................. A61B 1/30
[52] U.S. Cl. ...................................................... 128/7
[58] Field of Search .................................. 128/7, 4, 6

[56] References Cited

U.S. PATENT DOCUMENTS

| | | | |
|---|---|---|---|
| 1,995,196 | 3/1935 | Wolf | 128/7 |
| 4,483,326 | 11/1984 | Yamaka et al. | 128/4 |
| 4,589,404 | 5/1986 | Barath et al. | 128/7 X |
| 4,615,332 | 10/1986 | Buess et al. | 128/6 |

FOREIGN PATENT DOCUMENTS

| | | | |
|---|---|---|---|
| 455836 | 4/1949 | Canada | 128/7 |
| PCT/USA86-/01022 | 5/1985 | PCT Int'l Appl. | |

OTHER PUBLICATIONS

W. B. Allan, "Fiber Optics Theory and Practice", *Optical Physics and Engineering, Series* Editor William L. Wolfe, Plenus Press, 1973, pp. 148–176.

Denise Grady, "The Artery Zapper", *Discover*, Dec. 1982, pp. 36–40.

Yoshikatsu Tanahashi, M.D., et al., "Percutaneous Laser Lithotripsy for Renal Calculi", *The Use of Laser Beam in Urology* 7th Report, 1984, pp. 125–126.

Yoshikatsu Tanahashi, M.D., "Percutaneous Laser Lithotripsy for Renal Calculi", Preprint–Duplicate of 7th Report, pp. 1–5, 1983.

Yoshikatsu Tanahashi, M.D., "Transurethral Disintegration of Urinary Calculi by the Use of Laser Beam", Urology, vol. 10, pp. 30–33 (1981).

Flyer from Biomedical Business International, Tustin, CA, pp. 196–197, Dec., 1983.

Flyer on Karl Storz Endoscope (1987).

Richard Wolfe Medical Instruments Catalog, III.87, pp. D31, D33 (1987).

*Primary Examiner*—William H. Grieb
*Attorney, Agent, or Firm*—Hamilton, Brook, Smith & Reynolds

[57] ABSTRACT

An endoscope provides a tube which is rigid enough along its length to be displaced by axial and rotational translation through open regions. The tip end of the tube is laterally flexible relative to the length of the tube. Wires connected to opposite sides of the flexible tip provide user control of the flexing of the tip. The sufficiently rigid length, flexible tip and dimensions of the tube enable placement of the tip end adjacent to kidney stones lodged in the ureter and calyxes of the kidney. The flexible tip further enables atraumatic use of the device. The tube may be multi-channeled to enable a view of the body canals and target stones in one channel, and to carry laser radiation by means of laser delivering fiber to the stones in another channel. Fiber optics may be employed between channels or within a channel of the tube to aid in the viewing of the pertinent body areas.

39 Claims, 2 Drawing Sheets

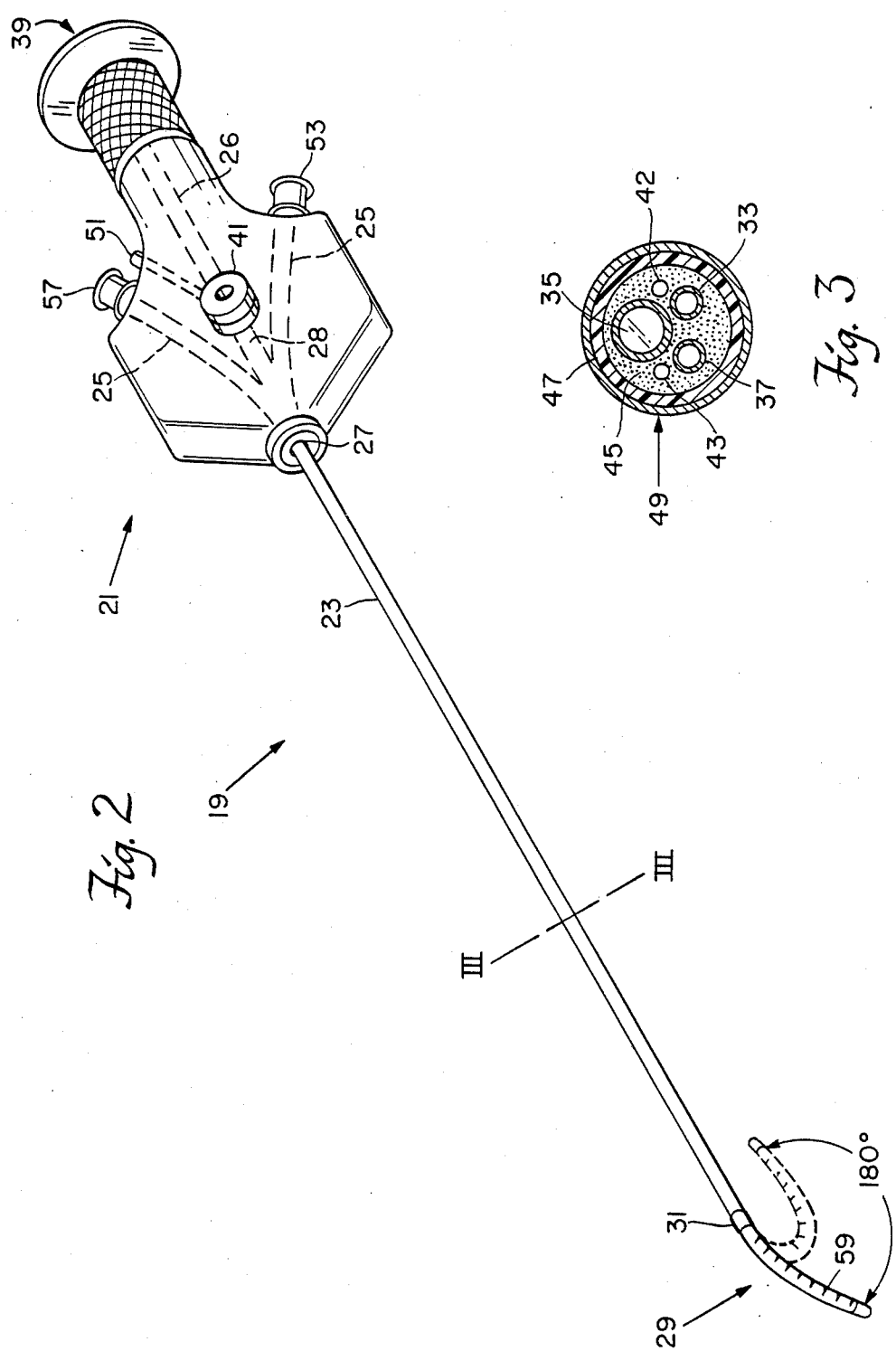

RIGID ENDOSCOPE WITH FLEXIBLE TIP

BACKGROUND OF THE INVENTION

The invention disclosed herein pertains to an endoscope used to visualize the urinary system. As shown in FIG. 1, kidneys 13 of the human body are connected to a bladder 9 by very narrow ducts called ureters 11 The openings of the ureters 11 into urinary bladder 9 are about 1 to 4 mm wide. Bladder 9 is partially surrounded from behind by pelvis 15 which serves as a protective shield for the bladder. The natural flow of body fluids is from the kidneys 13 through ureters 11 into bladder area 9 and is discharged from the body through urethra 17. The opening of the urethra to release fluids from the body is about 5 mm to 10 mm wide.

Urinary bladder stones 8 and kidney stones 7 have been known to become lodged in the bladder 9 and ureters 11 as well as in calyxes 5 of the kidney 13 respectively. This causes blockage of flowing body fluids and is very painful. Various medical devices have been developed to remove bladder stones 8, and/or kidney stones 7. The devices for removing the latter are pertinent to the general subject matter of the present invention.

The medical devices which have been developed to remove kidney stones generally involve a multi-channeled device called a ureteroscope. The ureteroscope is positioned within the body (i.e. urethra 17, bladder 9 and ureter 11) and has working channels which provide access to and from the areas where kidney stones 7 are lodged. A typical ureteroscope is rigid along its length so as to enable axial and rotational translation in the urethra 17 and bladder 9 areas. Typically, the rigid ureteroscope is greater than 3 mm in diameter and therefore unable to fit through most openings into ureters 11 in their natural size. Ureters 11 can be mechanically dilated to accommodate the rigid ureteroscope This dilation is however traumatic to the body, even though it may not be symptomatically apparent. Even after entering the ureter 11, the rigid ureteroscope is unable to bend toward the kidney stones 7 lodged in calyxes 5 of kidneys 13. Furthermore, the tip end of the rigid ureteroscope tends to penetrate the surrounding body tissue during use and is therefore considered to be traumatic to the body.

A flexible ureteroscope has been developed to serve the same purpose as the rigid ureteroscope. The flexible ureteroscope is guided by a rigid cylindrical tube called a cystoscope which is positioned in the bladder 9 through the urethra 17. The flexible ureteroscope is inserted into the cystoscope which guides the flexible ureteroscope to the bladder 9 and into the ureter 11. The cystoscope is too large in diameter to enter the ureter 11. Thus, the flexible ureteroscope must be maneuvered past the end of the rigid cystoscope and into the opening of the ureter 11 from the bladder 9. This requires the user of the device to stabilize the rigid cystoscope while maneuvering the flexible ureteroscope from an end opposite the target end. Further, the flexible tube of the ureteroscope is so flexible that it tends to coil at the opening to the ureter 11 (especially when the opening is tight) once outside the end of the rigid cystoscope and is not easily maneuvered by the pushing action of the user from the opposite end. In addition, a rotational torque can not be easily transmitted to the target or tip end of the flexible ureteroscope. On the other hand the tip end of the flexible ureteroscope is less traumatic to the body than the tip end of the rigid ureteroscope.

Employed within a working channel of the flexible and/or rigid ureteroscopes are various mechanical accessories for engulfing and retrieving, or grasping and crushing kidney stones 7. Also, a rigid ultrasound probe for delivering ultrasound waves to break the kidney stones 7 has been developed to be employed in a working channel of a rigid ureteroscope. Further, an electrohydraulic generator has been developed to generate a spark at the tip end of a flexible or rigid ureteroscope to break target kidney stones 7 which are positioned adjacent to the tip end of the ureteroscope.

Recently, "extracorporeal acoustic shock wave" therapy has been used to break kidney stones into particles which are small enough to pass through the ureter and urethra by natural means. This therapy entails the immersion of the patient in a bath of water. Shock waves are generated in the water and focused toward the areas where target kidney stones are lodged. The waves penetrate the body from the outside and break the target stones. However, such acoustic shock wave therapy or treatment does not affect kidney stones which are lodged in the lower region of ureters 11 and protected by the surrounding pelvis 15.

More recently, the Candela Laser Corporation dye laser has been developed to apply a photoacoustic effect to kidney stones 7 which are lodged in areas protected by the pelvis 15 and in other areas. Such an effect breaks the stones into particles which are small enough to pass through the ureter and urethra.

SUMMARY OF THE INVENTION

The present invention provides an improved ureteroscope for, among other uses, carrying a laser fiber to deliver laser light from a laser source to a target kidney stone. More generally, the present invention provides a ureteroscope which is rigid enough to provide both axial and rotational translation along its length to be easily maneuvered into the ureter and has a user deflectible tip which enables a wider view angle and readily follows curves of body canals to provide atraumatic operation.

In particular, the present invention provides an endoscope having a shaft which is rigid enough along its length to enable displacement through axial and rotational translation with the maneuvering of one end of the shaft. At the opposite end (i.e. the target end) of the shaft is a flexible tip portion which is laterally moveable relative to the length of the shaft.

In a preferred embodiment, the shaft comprises a plastic hose jacketed by a metallic (i.e. stainless steel) cylindrical tube. The finished outer diameter is less than about 3 mm. The tip portion is user moveable by a set of wires connected to the tip portion and leading through the plastic hose to a handle end of the shaft which is opposite the target end of the shaft.

In addition, the shaft may be multi-channeled. One channel is for viewing through from the handle end of the shaft to subjects outside the tip portion of the shaft. A second channel is for carrying laser delivering fiber to the subject stones adjacent to and outside the tip portion.

Light from an external source, through fiber optics or the like, running between the channels of the tube aid in the viewing of the subject. Alternatively light carrying fiber optics or the like may be positioned within a channel of the tube.

Other channels may be used to pass fluids to and from the ureter 11 and bladder area 9.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a schematic view of an endoscope embodying the present invention.

FIG. 3 is a cross section of the endoscope of FIG. 2 through line III—III.

DETAILED DESCRIPTION OF THE PREFERRED EMBODIMENT

Figure 1:
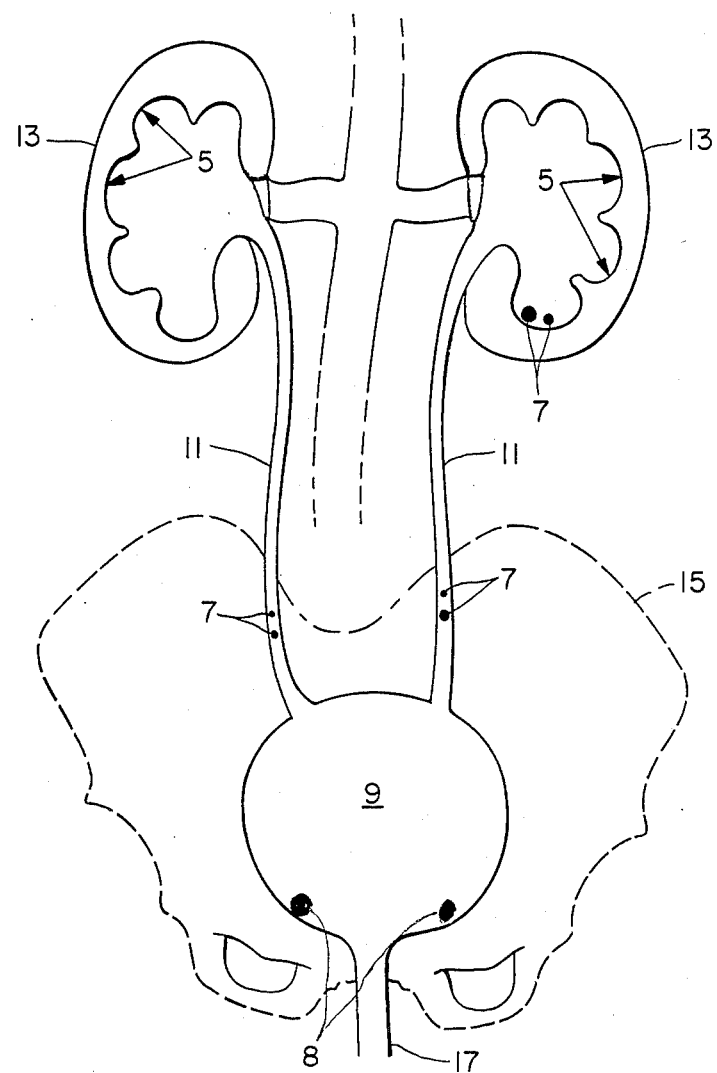
FIG. 1 is a schematic view of the bladder area of a human body.

An endoscope embodying the present invention is provided in FIG. 2. The endoscope 19 has a handle 21 connected to one end of a main tube or hollow shaft 23. The handle has numerous bores 25, 26 and 28 which converge at a common aperture 27. Each bore 25, 26 and 28 opens on a different side of handle 21. The main tube 23 is connected on one end to the common aperture 27 and has a flexible tip 29 on an opposite end. Flexible tip 29 is user deflectible by controls in handle 21 to be described. Preferably, flexible tip 29 is laterally deflectible 180° to one side of the longitudinal axis of main tube 23.

Main tube 23 is about 35 to 65 cm long and has an outer diameter of about 3 mm or less. Flexible tip 29 has an outer diameter of about 3 mm or less and a length of up to about 12 cm. Main tube 23 is sufficiently flexible along its length to follow various canals of the human body such as the urethra 17 and ureter 11 shown in FIG. 1. The length of main tube 23, however, is rigid enough to enable axial and rotational translation with the maneuvering of the handle 2; without uncontrolled twisting and coiling in the open region of the bladder. Hence, the user is able to insert main tube 23, leading with tip end 29, into the urethra 17 area and maneuver the endoscope through bladder area 9 in such a way that the flexible tip end 29 reaches and enters the opening of ureter 11. The deflection of tip end 29 upon user command aids the user in finding the opening of ureter 11 with tip end 29 and in positioning tip end 29 in the opening. In addition, the small diameter of flexible tip end 29 allows the user to insert flexible tip 29 into the narrow opening of ureter 11 and through the ureter 11 to kidney 13.

Further, the flexible tip end 29 being laterally deflected upon user command enables atraumatic use of the device and precise positioning of the tip end 29 adjacent to the kidney stones 7 of interest once inside ureter 11 and kidney 13. Especially, the flexible tip end 29 enables the user to view and deliver laser energy to kidney stones 7 in the different calyxes 5 of the kidney 13.

In a preferred embodiment, main tube 23 is multi-channeled as shown in the cross section of FIG. 3. The bores in handle 21 lead to respective channels of the main tube 23 which continue through similar channels in flexible tip end 29. In one design, flexible tip end 29 is a separate multi-channel piece which is connected to main tube 23 by a metallic joint 31. Joint 31 provides tapered matching channels where the channels on one end have diameters equal to diameters of respective main tube channels and the joint channels on the opposite end have diameters matching that of the flexible tip channels. Such tapering provides a smooth continuation of the channels and prevents "step change" of the media flowing through the channels from the handle end to the tip end.

Bore openings 53, 57 shown in FIG. 2 on different sides of handle 21 lead to working channels 33 and 37 respectively of FIG. 3. One working channel 33 (37) is used to carry laser radiation provided by a dye laser. In a preferred embodiment, a laser carrying fiber from a Candela Laser Corp. dye laser is inserted through bore opening 53 (57) into working channel 33 (37). When flexible tip end 29 is positioned adjacent to a target stone 7, the dye laser is activated and laser radiation is transferred through the working channel to the stone. The other working channel 37 (33) carries fluids to and from the body.

Bore opening 39 leads to image carrying channel 35 of FIG. 3 through which the body canals and target stones 7 are viewed. That is, the user looks through bore opening 39, while maneuvering main tube 23 within the body by handle 21, to view his way through the pertinent body canals (i.e. urethra, bladder area, ureter and kidney) and to locate target stones 7. A view of the respective area is conveyed through image channel 35 from flexible tip end 29 through main tube 23, to bore 26 in handle 21 and out bore opening 39. Preferably, image channel 35 and bore 26 carry a coherent bundle of fiber optics.

To aid in this viewing, light is provided through the endoscope 19 by fiber optics or other light sources. Fiber optics 45 may be inserted into bore 28 through bore opening 41 in handle 21 which leads to areas between the channels of main tube 23 as shown in FIGS. 2 and 3. The fiber optics 45 reach tip end 29 and provide enough light to enable a clear view of the subject area. Further, fiber optics are bendable with flexible tip end 29. Alternatively, fiber optics may be positioned within image channel 35.

The channels 33, 35, and 37 are preferably cylindrical, plastic or non-metallic tubings. The channels are bound together within a plastic (i.e. polyurethane) cylindrical tubing 47 shown in FIG. 3. An outer casing 49, another cylindrical tubing, preferably of stainless steel, covers the plastic tubing 47. To minimize the total diameter, a plastic tubing 47 of diameter about 2.67 mm and an outer casing 49 of about 3.17 mm is preferred.

Flexible tip 29 comprises a plastic outer tubing (i.e. polyurethane) which houses the channels previously discussed. As shown in FIG. 2, outer opposite sides of the tip end 29 have a series of lateral notches 59 cut into the sides to enable lateral deflection as is known in the art. One of the series of notches 59 lies across the side of tip end 29 toward which tip end 29 deflects. Two stainless steel spring guide wires 42, 43 within the plastic tubing are attached, one each to the notched sides of tip 29. The spring guide wires 42, 43 lead through main tube 23 to control 51 at handle 21 as shown in FIGS. 2 and 3. When the user moves the control 51 in one direction, one spring guide wire 43(42) is placed under tension and pulls tip end 29 to the side to which that spring guide wire is attached. When the user moves control 51 in an opposite direction, the second spring guide wire 42 (43) is placed under tension and the other spring guide wire 43(42) is released. Flexible tip 29 then straightens to the side to which the second spring guide wire 42(43), now tensioned, is attached.

By rotating handle 21 180°, the flexible tip 29 is brought to an opposite portion of the plane in which it was being flexed. Note that such rotation is made possible by the rigidity of main tube 23. The flexible tip 29 can then be flexed 180. to one side in this portion of a plane by control 51 in a manner similar to that previously described. In this fashion, flexible tip 29 can be flexed through 360° and provide any necessary angle of view.

Other means for flexing the tip end 29 may be used. In the above described method, additional wires may be connected to other sides of the flexible tip end and the tip end may have notches along those other sides to provide lateral flexing in more than two directions.

In another design of control 51 for laterally flexing tip end 29, a lock and release scheme may be employed. In such a scheme, control 51 may be locked in place once the user has positioned it to provide a desired angle of deflection of tip end 29. In order to subsequently change the position of control 51, and thus the angle of deflection of tip end 29, control 51 must be unlocked or released. Thus, this scheme provides stabilization of control 51 and flexible tip end 29 once control 51 is positioned as desired.

It is understood that other materials and dimensions may be used for the endoscope of the present invention keeping in mind the dimensions of the affected body parts. Further, the number and dimensions of the channels employed are variable depending on the accessories (i.e. dye laser, fiber optics, etc.) used in conjunction with the endoscope. Alternatively, other shaped handles and handles of other designs may be used.

While the invention has been particularly shown and described with reference to embodiments thereof, it will be understood by those skilled in the art that various changes in form and details may be made therein without departing from the spirit and scope of the invention as defined by the appended claims.

I claim:
1. An endoscope comprising:
   a tube having (i) a length which is sufficiently rigid such that the tube is evenly displaced along its length through axial and rotational translation by maneuvering one end of the tube, and (ii) a tip portion at an opposite end of the tube having an outer diameter of less than about 3 mm and a length of up to about 12 cm and comprising a notched plastic tubing, the tip portion being selectively flexible up to about 180° relative to the length by user control while maintaining the length substantially stationary; and
   means for laterally moving the tip portion relative to the length of the tube.
2. An endoscope as claimed in claim 1 wherein the tube comprises metallic covered plastic along its length and has an outer diameter of about 3 mm or less at areas which comprise the metallic covered plastic.
3. An endoscope as claimed in claim 1 wherein the means for moving the tip portion includes a plurality of wires connected to different sides of the tip portion.
4. An endoscope as claimed in claim 1 wherein the tube is multichanneled, one channel for viewing through from the one end to objects outside the tip portion, a second channel for carrying laser radiation to objects outside the tip portion.
5. An endoscope as claimed in claim 4 wherein a coherent fiber optic bundle is fixed within the one channel.
6. An endoscope as claimed in claim 4 further comprising illuminating light means positioned inside the tube for delivering illuminating light to the tip portion of the tube.
7. An endoscope as claimed in claim 6 wherein the illuminating light means includes fiber optics.
8. An endoscope as claimed in claim 4 wherein other channels are used for passage of fluids and instruments.
9. An endoscope as claimed in claim 1 wherein the tube is multichanneled.
10. An endoscope comprising:
    a handle having a plurality of bores with respective opening ends on different sides of the handle and opposite ends converging at a common aperture in the handle;
    a multi-channeled tube having one end connected to the handle aperture, one channel for viewing through from an opening end of one bore of the handle to an opposite end of the tube, a second channel for carrying laser radiation to the opposite end of the tube, the tube being rigid enough along its length such that it is evenly axially and rotationally translateable along its length;
    light means positioned within the tube for delivering illuminating light to the opposite end of the tube; and
    a selectively flexible tip piece having one end connected to the opposite end of the tube and an open end opposite the one end, the flexible tip having an outer diameter of less than about 3 mm and a length of up to about 12 cm and comprising a notched plastic tubing enabling flexing up to about 180° relative to the length of the tube without bending of the tube, the flexible tip having multi-channels adapted to the channels of the tube to provide continuations of the view through one channel, the laser radiation in the second channel and illuminating light from the light means to the open end, the flexible tip being user deflectible to provide different angles of view and delivery of laser radiation through the device.
11. An endoscope as claimed in claim 10 wherein a coherent fiber optic bundle is fixed within the one channel.
12. An endoscope as claimed in claim 10 wherein the multi-channeled tube comprises metallic material and plastic and has a length of about 33 cm to about 65 cm and an outer diameter of less than about 3 mm at areas which comprise the metallic material and plastic.
13. An endoscope as claimed in claim 10 wherein the channels of the flexible tip are tapered having smaller diameters at the open end of the tip than at the end connected to the tube.
14. An endoscope as claimed in claim 10 wherein the light means includes fiber optics.
15. An endoscope as claimed in claim 10 wherein other channels are used for passage of fluids and instruments.
16. A device for delivering laser radiation to a target object comprising:
    a multi-channelled tube having a tip end directed toward the target, one channel for viewing the target from an end of the tube opposite the tip end, a second channel for carrying laser radiation to the target, the tip end being selectively flexible by user control and a remaining length of the tube being substantially rigid such that the tube is both axially and rotationally translateable evenly from the opposite end to the tip end; and means for laterally moving the tip end up to about 180° relative to the remaining length of the tube without bending the tube along the remaining length, the tip end having an outer diameter of less than about 3 mm and a length of up to about 12 cm.

17. A device as claimed in claim 16 wherein the means for laterally moving the tip end includes user controls in a handle connected to the opposite end of the tube.

18. A device as claimed in claim 16 wherein the tube has a outer diameter of about 3 mm or less.

19. A device as claimed in claim 16 wherein the tube comprises metal and plastic.

20. A device as claimed in claim 16 wherein the channels are tapered toward the tip end.

21. A device as claimed in claim 16 further comprising light means positioned within the tube to provide light with which to view the target.

22. A device as claimed in claim 21 wherein said light means include fiber optics.

23. A device as claimed in claim 21 wherein said light means includes fiber optics positioned within the one channel for viewing the target.

24. An endoscope as claimed in claim 16 wherein a coherent fiber optic bundle is fixed within the one channel.

25. A method for breaking kidney and bladder stones the steps comprising:

providing a multi-channeled tube having a length which is sufficiently rigid such that it is both axially and rotationally translated by one end of the tube and having a selectively flexible tip end opposite the one end and controllable from the one end, the flexible tip end having an outer diameter of less than about 3 mm and a length of up to about 12 cm and comprising a notched tubing;

viewing body canals leading to the stones through one channel in the tube from the one end;

positioning the flexible tip end adjacent to the stones by maneuvering the one end of the tube and by flexing the tip end laterally up to about 180° relative to the length of the tube without bending the tube along its length; and transferring laser radiation through a second channel in the tube from the one end to the stones adjacent to the selectively positioned tip end.

26. A method as claimed in claim 25 further comprising the step of providing illuminating light means through a channel of the tube.

27. A method as claimed in claim 26 wherein the illuminating light means includes fiber optics.

28. An endoscope comprising:

a tube having a length which is sufficiently rigid such that the tube is evenly displaced along its length through axial and rotational translation by maneuvering one end of the tube;

a coherent fiber optic bundle fixed within the tube for providing at the one end as seen through the tube an image of objects lying outside an opposite end of the one end;

a tip portion of the tube at the opposite end having an outer diameter of less than about 3 mm and a length up to about 12 cm and comprising a notched plastic tubing, the tip portion being selectively flexible relative to the length by user control; and means for laterally moving the tip portion up to about 180° relative to the length of the tube without bending the tube along its length.

29. An endoscope as claimed in claim 28 wherein the tube comprises metallic covered plastic along its length and has an outer diameter of about 3 mm or less at areas which comprise the metallic covered plastic.

30. An endoscope as claimed in claim 28 wherein the tube is multi-channeled, one channel for carrying laser radiation to objects outside a target end opposite the one end.

31. An endoscope as claimed in claim 30 further comprising illuminating light means positioned inside the tube for delivering illuminating light to the target end of the tube.

32. An endoscope as claimed in claim 31 wherein the illuminating light means includes fiber optics.

33. An endoscope as claimed in claim 30 wherein other channels are used for passage of fluids and instruments.

34. An endoscope as claimed in claim 28 wherein the means for moving the tip portion includes a plurality of wires connected to different sides of the tip portion.

35. An endoscope comprising:

a tube having (i) a length which is sufficiently rigid such that the tube is substantially evenly displaced along its length through axial and rotational translation by maneuvering one end of the tube, and (ii) a tip portion at an opposite end of the tube which is controllably flexible relative to the length, the tip portion having an outer diameter of less than about 3 mm and a length of up to about 12 cm and comprising a notched plastic tubing enabling flexing of the tip portion up to about 180° relative to the tube length without bending along the tube length.

36. An endoscope as claimed in claim 35 wherein the tube has an outer diameter of about 3 mm or less at are as along its length which comprise metallic covered plastic.

37. An endoscope as claimed in claim 35 wherein the tube is multichanneled, one channel for viewing through from the one end to objects outside the tip portion, a second channel for carrying laser radiation to objects outside the tip portion.

38. An endoscope as claimed in claim 37 wherein other channels are used for passage of fluids and instruments.

39. An endoscope as claimed in claim 37 wherein a coherent fiber optic bundle is fixed within the one channel.

* * * * *

UNITED STATES PATENT AND TRADEMARK OFFICE
CERTIFICATE OF CORRECTION

PATENT NO. : 4,802,461
DATED : February 7, 1989
INVENTOR(S) : George Cho and Horace Furumoto It is certified that error appears in the above—identified patent and that said Letters Patent is hereby corrected as shown below:

On the cover page of the patent, the name of the second inventor has been omitted.  Under "Inventor:", after "Sudbury,", the name ---Horace Furumoto, Wellesley, all of--- should be inserted.

Column 8, line 48, after "are", insert a hyphen.

Signed and Sealed this

Fifteenth Day of August, 1989

Attest:

DONALD J. QUIGG

Attesting Officer

Commissioner of Patents and Trademarks